(12) United States Patent
Yoshimura et al.

(10) Patent No.: US 8,739,556 B2
(45) Date of Patent: Jun. 3, 2014

(54) CRYOPRESERVATION DEVICE

(75) Inventors: Shigehiro Yoshimura, Yokohama (JP); Hidetoshi Ohta, Kofu (JP); Mamoru Fujita, Kai (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 300 days.

(21) Appl. No.: 13/003,940

(22) PCT Filed: Nov. 11, 2008

(86) PCT No.: PCT/JP2008/070496
§ 371 (c)(1),
(2), (4) Date: Jan. 13, 2011

(87) PCT Pub. No.: WO2010/044172
PCT Pub. Date: Apr. 22, 2010

(65) Prior Publication Data
US 2011/0120148 A1 May 26, 2011

(30) Foreign Application Priority Data

Oct. 17, 2008 (JP) .............................. P2008-268770

(51) Int. Cl.
*F25B 19/00* (2006.01)
(52) U.S. Cl.
USPC ............................................ 62/51.1; 62/378
(58) Field of Classification Search
USPC ............... 62/48.1, 51.1; 901/27; 220/560.04, 220/560.12
See application file for complete search history.

(56) References Cited

U.S. PATENT DOCUMENTS

| 3,168,362 | A | * | 2/1965 | Perkins | ......................... | 312/400 |
| 3,904,037 | A | * | 9/1975 | Alter | ............................. | 206/534 |
| 4,537,034 | A | * | 8/1985 | Crouch | ............................. | 62/62 |

(Continued)

FOREIGN PATENT DOCUMENTS

| JP | 4-15911 | 2/1992 |
| JP | 6-167431 | 6/1994 |
| JP | 2002-214227 | 7/2002 |
| JP | 2005-143873 | 6/2005 |

(Continued)

OTHER PUBLICATIONS

Fischer Scientific Nalgene Inc. Cryosleeves. Taken from http://chromatography-online.co.uk/catalog/nalgene-labware-polyvinyl-chloride-cryosleeve-50160001-p-2566.html, Nov. 30, 2008.*

(Continued)

*Primary Examiner* — John Pettitt
*Assistant Examiner* — Tareq M Alosh
(74) *Attorney, Agent, or Firm* — Nixon & Vanderhye, P.C.

(57) ABSTRACT

A cryopreservation device of the present invention includes: a cryopreservation vessel; a house which houses the cryopreservation vessel; and a handling robot provided on the house, wherein the cryopreservation vessel comprises a vessel body which holds a low-temperature liquefied gas, a cap which closes an opening section of the vessel body and has a plurality of insertion holes formed to pass through in a vertical direction, and ampoule storing tools which are housed so as to be able to pass through the insertion holes of the cap, in which the ampoule storing tools are each comprised of a support pillar and a plurality of ampoule storing sections which are attached to the support pillar so as to be arrayed in a vertical direction of the support pillar, and an ampoule-putting-in/out work hole is formed in the cap so as to pass through in a vertical direction.

2 Claims, 9 Drawing Sheets

(56) References Cited

U.S. PATENT DOCUMENTS

| | | | |
|---|---|---|---|
| 5,233,844 A * | 8/1993 | Knippscheer et al. | 62/440 |
| 5,921,102 A * | 7/1999 | Vago | 62/337 |
| 6,641,042 B1 * | 11/2003 | Pierenkemper et al. | 235/462.01 |
| 6,925,815 B2 * | 8/2005 | Shafer | 62/51.1 |
| 7,162,888 B2 * | 1/2007 | Shu et al. | 62/378 |
| 7,527,764 B2 * | 5/2009 | Angelantoni et al. | 422/65 |
| 2004/0199142 A1 * | 10/2004 | Reilly | 604/523 |
| 2006/0222802 A1 * | 10/2006 | Stevens et al. | 428/40.1 |
| 2011/0181875 A1 * | 7/2011 | Nakahana et al. | 356/246 |

FOREIGN PATENT DOCUMENTS

| | | |
|---|---|---|
| JP | 2005-156136 | 6/2005 |
| JP | 2007-271279 | 10/2007 |
| JP | 2008-285181 | 11/2008 |

OTHER PUBLICATIONS

International Search Report for PCT/JP2008/070496, mailed Feb. 17, 2009.

* cited by examiner

CRYOPRESERVATION DEVICE

This application is the U.S. national phase of International Application No. PCT/JP2008/070496, filed 11 Nov. 2008, which designated the U.S. and claims priority to Japanese application no. 2008-268770, filed 17 Oct. 2008, the entire contents of each of which are hereby incorporated by reference.

TECHNICAL FIELD

The present invention relates to a cryopreservation device used to cryopreserve biological samples such as spermatozoa, embryo, and cells of animals.

Priority is claimed on Japanese Patent Application No. 2008-268770, filed Oct. 17, 2008, the content of which is incorporated herein by reference.

BACKGROUND ART

Examples of the prior arts regarding the cryopreservation device include Japanese Unexamined Patent Application, First Publication No. 2005-143873, Japanese Unexamined Patent Application, First Publication No. 2005-156136, and Japanese Unexamined Utility Model Application, First Publication No. Hei 4-15911.

In one of these prior arts, (1) the conformation is adapted, in which a lot of ampoules that include biological samples are stored in a plurality of storing sections of a storing box wherein the storing sections are partitioned, a plurality of these storing boxes are housed in a housing rack, and a plurality of these housing racks that each houses several hundreds to one thousand and several hundreds of ampoules are housed in a cryopreservation vessel that holds a low-temperature liquefied gas such as liquefied nitrogen.

Alternatively, (2) the conformation is adapted, in which a lot of straw tubes that encapsulate biological samples are stored in a plurality of storing sections of a canister wherein the storing sections are partitioned, and a plurality of these canisters that each stores several hundreds of straw tubes are housed in a cryopreservation vessel that holds a low-temperature liquefied gas such as liquefied nitrogen.

The cryopreservation vessels having the aforementioned conformations have the advantage in that it is possible to cryopreserve a lot of, i.e. several thousands of, ampoules and straw tubes that encapsulate cryopreserved samples. However, these cryopreservation vessels have the following disadvantages, and the solution has been desired.

1) In the case of taking out the ampoule or straw tube that encapsulates a target sample, one of the housing rack or canister shall be taken out from the cryopreservation vessel. Therefore, a lot of samples other than the target cryopreserved sample are exposed to an ambient temperature, and the samples suffer damage due to increase in temperature. In addition, the number of times the ampoule or straw tube suffers damage increases.

2) The weight of the one storing rack is several kilograms, and therefore, it becomes difficult to take it into or out of the cryopreservation vessel. Moreover, the housing rack or canister may fall down within the cryopreservation vessel, and the storing box may drop from the housing rack. In addition, the ampoule or straw tube may sink down to the bottom of the cryopreservation vessel so as not to be recovered.

3) It is impossible to detect the preservation position of the housing rack or canister inside from the outside of the cryopreservation vessel. In addition, the sample management is very complicated because a lot of ampoules are stored in the one housing rack or canister.

As one solving the aforementioned problems, the present applicants have already proposed the following cryopreservation vessel as disclosed in Japanese Patent Application No. 2007-130357.

Figure 9:
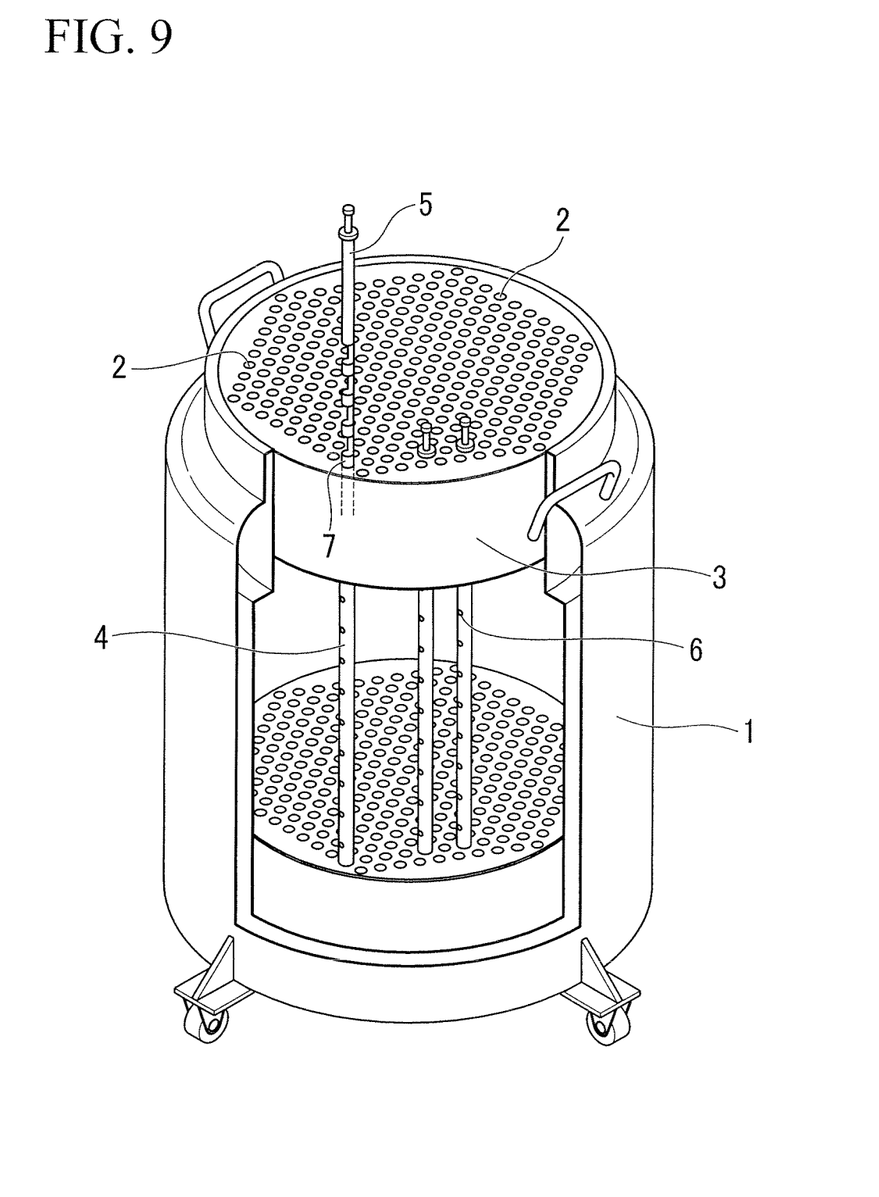
FIG. 9 is a schematic perspective view showing an example of a cryopreservation vessel, which is partially cut out, according to the invention of the prior application.

The cryopreservation vessel of the prior invention include, as shown in FIG. 9, a vessel body 1 which holds a low-temperature liquefied gas; a cap 3 which closes an opening section of the vessel body 1 and has a plurality of insertion holes 2 formed to pass through in a vertical direction (a thickness direction); sheath tubes 4 which are inserted into the insertion holes 2 of the cap 3; and ampoule storing tools 5 which are housed so as to be able to pass through the sheath tubes 4, wherein a plurality of gas permeable holes 6 are formed in each of the sheath tubes 4, and the ampoule storing tools 5 are each comprised of a support pillar and a plurality of ampoule storing sections 7 which are attached to the support pillar so as to be arrayed in a vertical direction of the support pillar and stores the ampoules.

In this cryopreservation vessel, the only several ampoules stored in the ampoule storing tool 5 can be taken out from the cryopreservation vessel. Moreover, especially when being stored in the ampoule storing section at the top of the ampoule storing tool, the required ampoule can be taken out without taking the other ampoules out from the cryopreservation vessel, and therefore, it is possible to prevent a lot of samples other than target sample from suffering damage due to increase in temperature.

When the ampoule is stored into or taken out from the cryopreservation vessel, it is unnecessary to remove the cap. Therefore, the evaporation amount of the low-temperature liquefied gas can be reduced.

In addition, the weight of the ampoule storing tools that store a plurality of the ampoules is reduced, and it is possible to reduce the operational burden during taking the ampoule storing tool into or out of the cryopreservation vessel.

Because the sample management can be carried out for each of the ampoules, it is possible to facilitate the complicated sample identification management and to confirm the preservation position of the ampoule from outside of the cryopreservation vessel.

Furthermore, there are the sheath tubes that pass through the cap of the cryopreservation vessel, and therefore, it is possible to prevent the sample loss due to the drop of the ampoule from the ampoule storing tool into the vessel.

Moreover, even when the ampoule drops within the sheath tube, the ampoule is held within the sheath tube, and therefore, the ampoule can be recovered by taking the sheath tube out from the cap.

However, in the cryopreservation vessel of the prior invention, an operator selects the target ampoule storing tool among a lot of ampoule storing tools with visual contact, pulls up it, and takes out the target ampoule among a plurality of ampoules stored in the ampoule storing tool by hand with visual contact.

For this reason, the identification of the ampoule storing tool and ampoule takes long time, and there is a possibility to confuse the ampoule storing tools and ampoules because of human work. Accordingly, there remain points to be improved.

[Patent Document 1]
Japanese Unexamined Patent Application, First Publication No. 2005-143873,

[Patent Document 2]
Japanese Unexamined Patent Application, First Publication No. 2005-156136,
[Patent Document 3]
Japanese Unexamined Utility Model Application, First Publication No. Hei 4-15911.

DISCLOSURE OF INVENTION

Problems to be Solved by the Invention

Therefore, an object of the present invention is to reduce the time required for the identification of the ampoule storing tools and ampoules and to prevent the confusion of the ampoule storing tools and ampoules during operation of a cryopreservation vessel including: a vessel body which holds a low-temperature liquefied gas; a cap which closes an opening section of the vessel body and has a plurality of insertion holes that are formed so as to pass through in a vertical direction; a sheath tube inserted into the insertion holes of the cap; and ampoule storing tools which are housed so as to be able to pass through the sheath tube, wherein the ampoule storing tools have a plurality of ampoule storing sections.

Means to Solve the Problems

In order to achieve the aforementioned objects,
the present invention is a cryopreservation device including:
 a cryopreservation vessel;
 a house which houses the cryopreservation vessel; and
 a handling robot provided on the house, wherein
 the cryopreservation vessel includes a vessel body which holds a low-temperature liquefied gas, a cap which closes an opening section of the vessel body and has a plurality of insertion holes formed to pass through in a vertical direction, and ampoule storing tools which are housed so as to be able to pass through the insertion holes of the cap, in which the ampoule storing tools are each comprised of a support pillar and a plurality of ampoule storing sections which are attached to the support pillar so as to be arrayed in a vertical direction of the support pillar, and an ampoule-putting-in/out work hole is formed in the cap so as to pass through in a vertical direction;
 the house is used to take the cryopreservation vessel therein or thereout, is adjacent to the opening section of the vessel body, and has a work table provided in the vicinity of the ampoule-putting-in/out work hole; and
 the handling robot includes a gripper head by which the certain ampoule storing tool is pulled out from the insertion hole, inserted into the ampoule-putting-in/out work hole, stopped at a predetermined position, pulled out from the ampoule-putting-in/out work hole, and inserted into the original insertion hole, an input apparatus in which an identification management number of a certain ampoule is input, a bar-code reader which is provided on the work table of the house and reads an identification management number of a bar-code attached to the ampoule, and a control apparatus which controls a movement of the gripper head on the basis of the identification management number of the bar-code of the certain ampoule from the input apparatus and compares the identification management number from the input apparatus with the identification management number from the bar-code reader.

In the present invention, it is preferable that the cryopreservation vessel further comprise sheath tubes inserted into the insertion holes of the cap, and the ampoule storing tools be housed so as to be able to pass through the sheath tubes.

Effect of the Invention

According to the present invention, when an identification management number of the target ampoule is input to the input apparatus, the gripper head of the handling robot operates and pulls out the ampoule storing tool that stores the target ampoule, inserts it into the ampoule-putting-in/out work hole, and shove it until the target ampoule is exposed from the opening edge of the ampoule-putting-in/out work hole, and then stops. At this time, the bar-code readers mounted to the work table read the bar-code of the ampoule. Meanwhile, the control apparatus compares the identification management number from the bar-code readers with the identification management number from the input apparatus, and output the indication in the case where the both are matched to one another. After the confirmation of this indication, an operator takes the target ampoule out from the ampoule storing tool.

Therefore, it is possible to automatically and promptly carry out the identification of the ampoule storing tools and ampoules, and to prevent the confusion of the ampoule storing tools and ampoules.

In addition, a series of the operations such as pulling out and the insertion of the ampoule storing tool are carried out by the gripper head of the handling robot. Thus, the burden of an operator is reduced, and workability is improved.

DESCRIPTION OF THE REFERENCE SYMBOLS

11 Cryopreservation vessel
12 House
13 Handling robot
14 Vessel body
15 Cap
16 Ampoule storing tool
17 Sheath tube 29 Insertion hole
29a Ampoule-putting-in/out work hole
31 Support pillar
34 Ampoule storing section
36 Ampoule
38a Work table
42 Robot body
43 Input apparatus
44 Control apparatus
46 Bar-code reader
58 Gripper head

BEST MODE FOR CARRYING OUT THE INVENTION

Cryopreservation Device

FIG. 1 to FIG. 8 shows one example of the cryopreservation device of the present invention.

Figure 1:
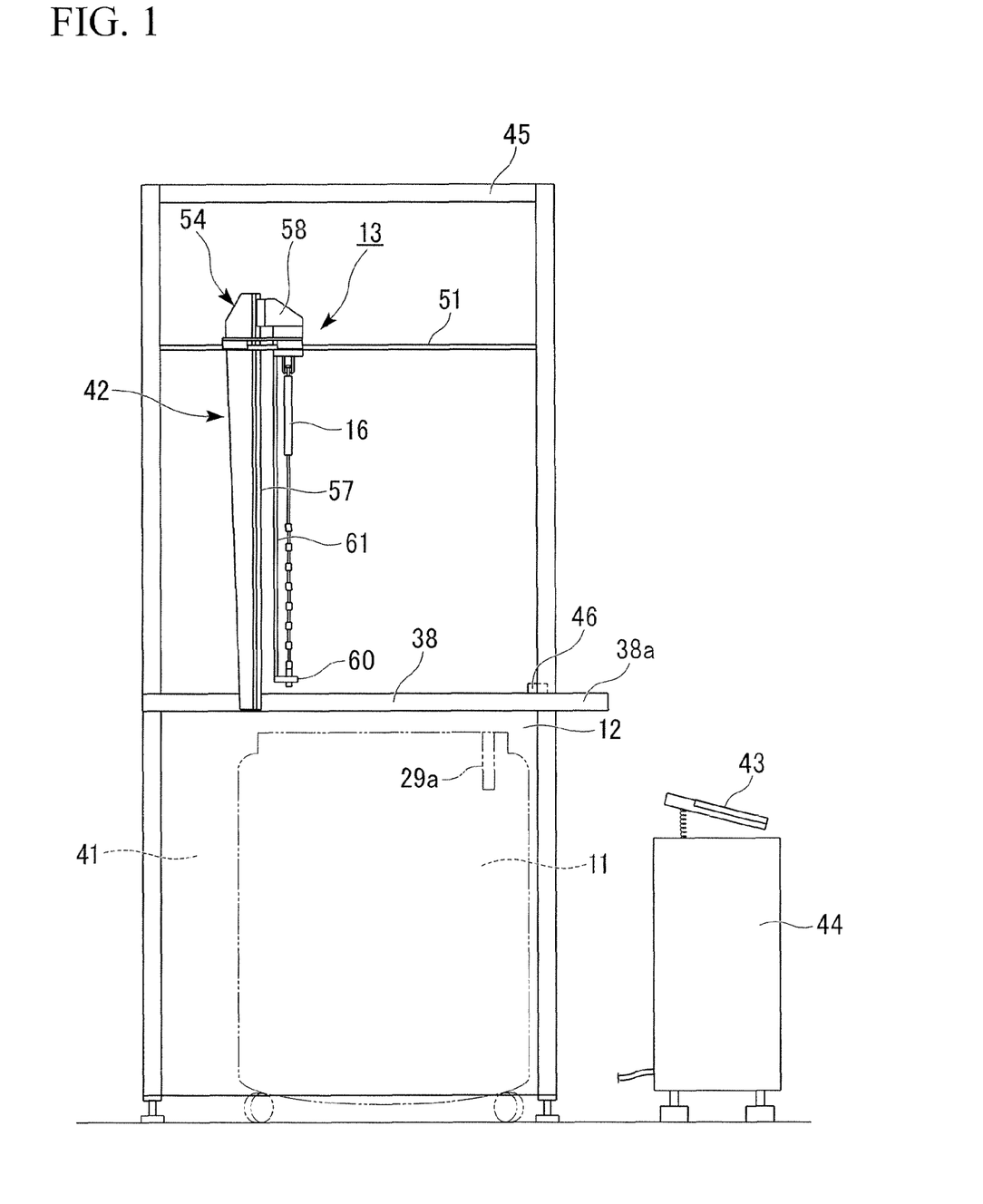
FIG. 1 is an entire schematic block diagram showing an example of the cryopreservation apparatus of the present invention.

As shown in FIG. 1, this cryopreservation device is schematically comprised of a cryopreservation vessel 11, a house 12 which houses the cryopreservation vessel 11 and a handling robot 13 provided on the house 12.
(Cryopreservation Vessel)

Figure 2:
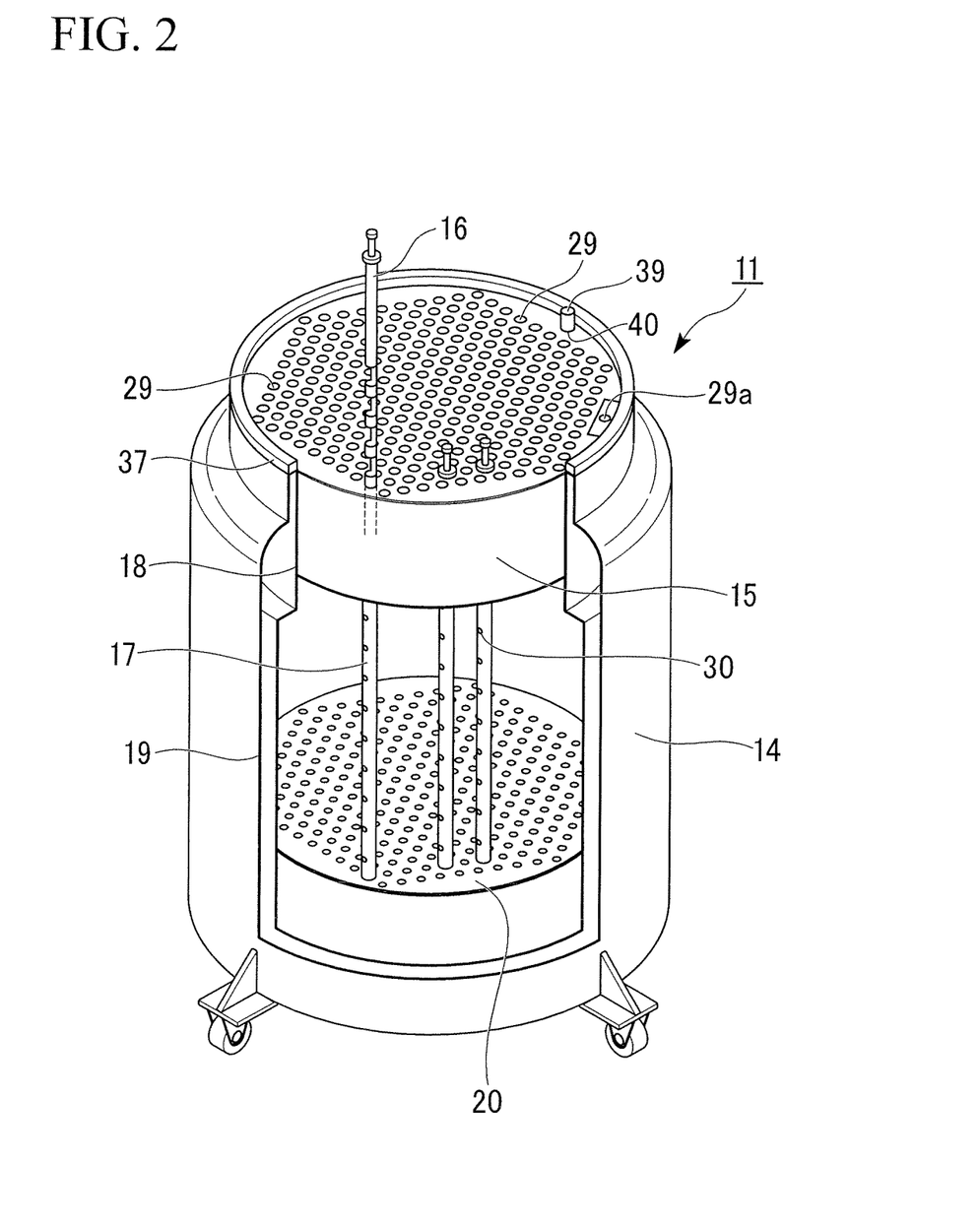
FIG. 2 is a schematic perspective view showing an example of the cryopreservation vessel, which is partially cut out, in the cryopreservation apparatus of the present invention.

As shown in FIG. 2, the cryopreservation vessel 11 is comprised of a vessel body 14, a cap 15, ampoule storing tools 16, and sheath tubes 17.

The vessel body 14 has a double structure formed of an inner vessel 18 and an outer vessel 19 made of stainless steel or the like, and is a vacuum thermal insulating vessel in which a space between the inner vessel 18 and the outer vessel 19 is vacuum.

A perforated plate 20 is mounted in the vicinity of the bottom portion of the inner vessel 18 of the vessel body 14, and the inner vessel 18 is to be filled close to the perforated plate 20 with the low-temperature liquefied gas such as liquefied nitrogen. The opening diameter of the opening section of the inner vessel 18 is made slightly smaller than the inner diameter of the body portion of the inner vessel 18, and the inner vessel 18 is formed into a so-called waistless pan shape.

Figure 3:
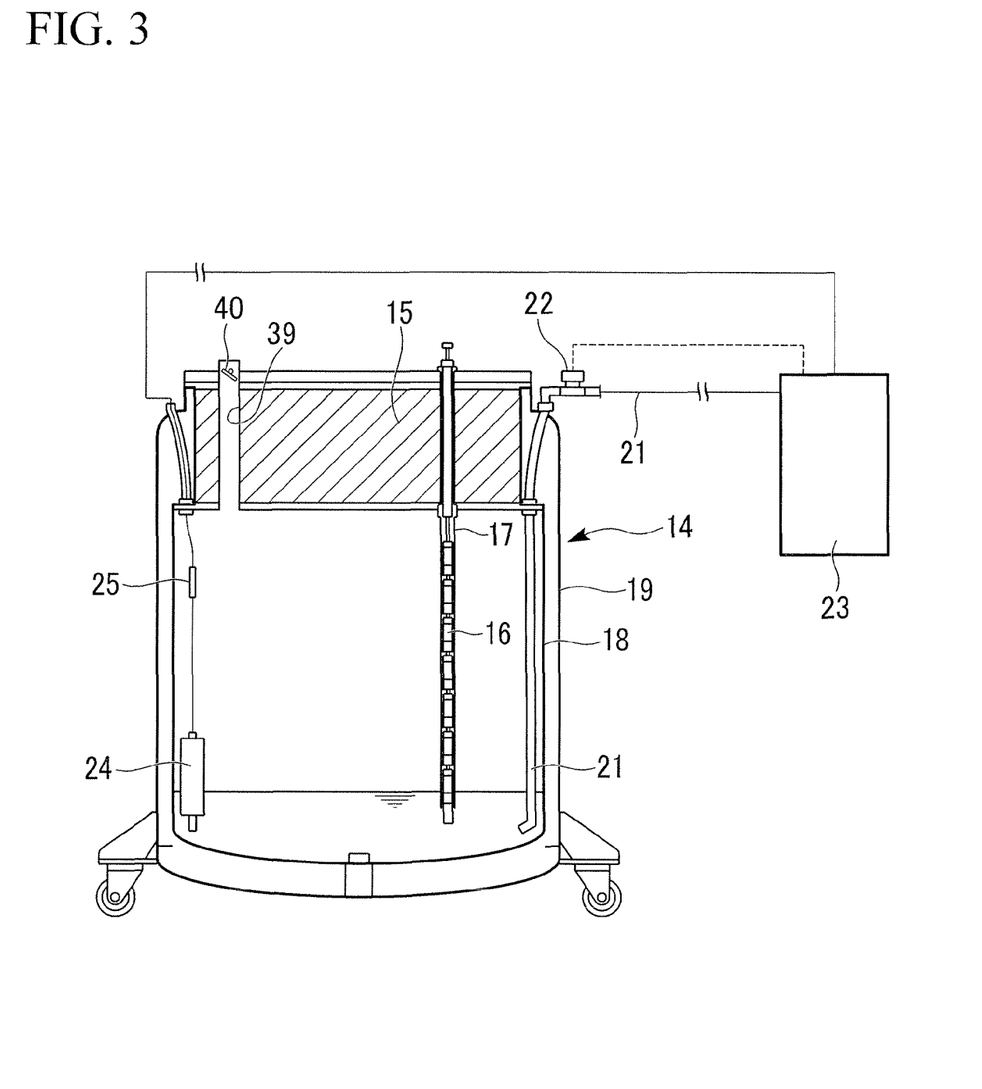
FIG. 3 is a schematic block diagram showing an example of the equipment for supplying a low-temperature liquefied gas to the cryopreservation vessel in the cryopreservation apparatus of the present invention.

Further, as shown in FIG. 3, a liquefied gas supply tube 21 for supplying or supplementing a low-temperature liquefied gas into the vessel body 14 is provided to the cryopreservation vessel 11. One end of the liquefied gas supply tube 21 passes through the side wall portion of the house 12 and the side wall portion of the vessel body 14, to extend close to the bottom portion of the inner vessel 18, and the other end thereof is connected to a liquefied gas supply source 23 via a flow regulating valve 22.

Moreover, as shown in FIG. 3, the vessel body 14 of the cryopreservation vessel 11 is equipped with a fluid level sensor 24 sensing a stored fluid level of the low-temperature liquefied gas and a temperature sensor 25 sensing a temperature of a vapor phase in the vessel body 14. Detection signals from these sensors 24, 25 are transmitted to the liquefied gas supply source 23, to control a point of supply time and an amount supplied of the low-temperature liquefied gas to be supplied into the vessel body 14.

Figure 4:
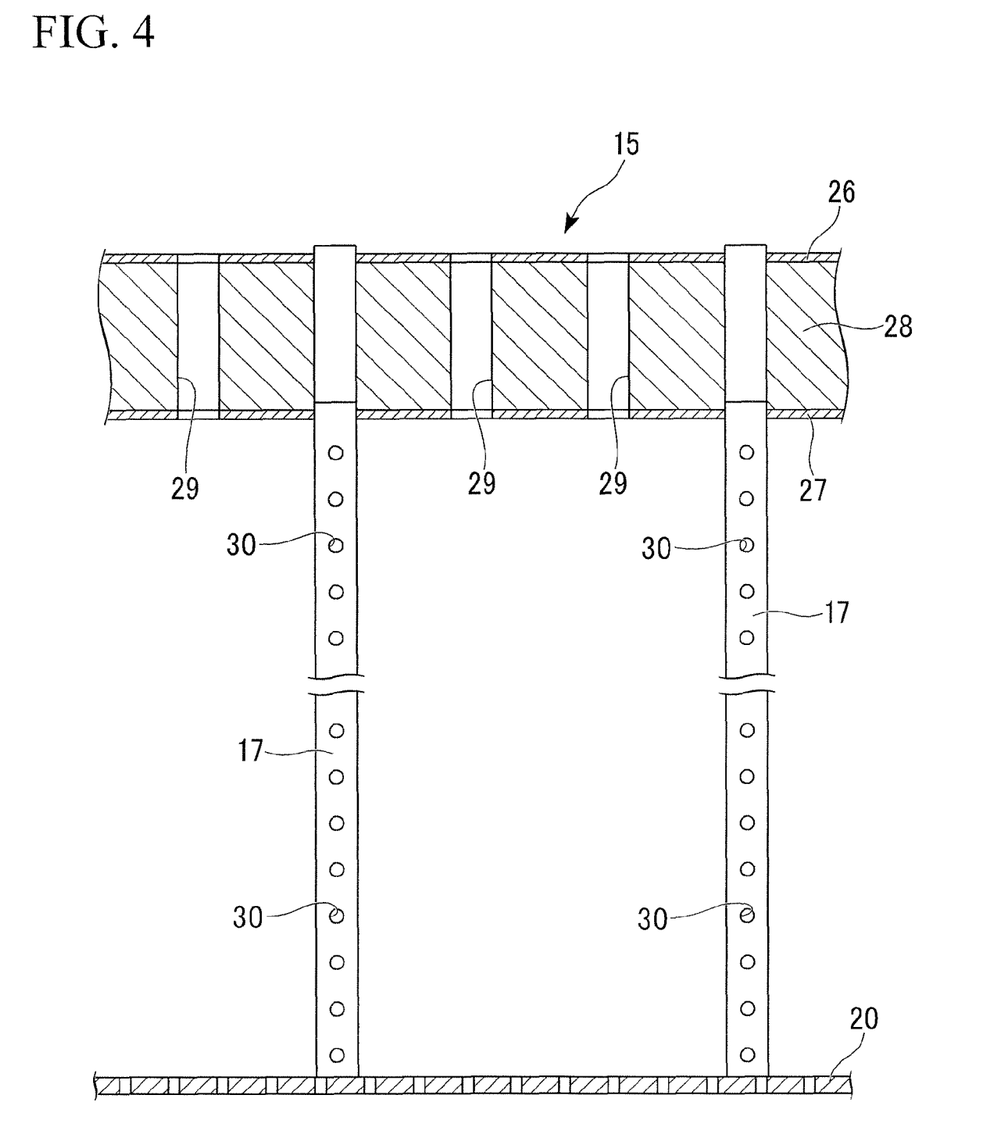
FIG. 4 is a schematic cross-sectional diagram showing an example of the cap and sheath tubes in the cryopreservation apparatus of the present invention.

The opening section of the inner vessel 18 of the vessel body 14 is configured to be closed so as to be openable and closable with the cap 15. As shown in FIG. 2, the cap 15 has a columnar shape whose outer diameter is approximately the same as the opening diameter of the opening section of the inner vessel 18. As shown in FIG. 4, the cap 15 is comprised of disk-shaped upper board 26 and lower board 27, and a thermal insulating body 28 made of a thermal insulating material such as an urethane resin foam therebetween, to have a thickness of approximately 200 to 300 mm, that is high in thermal insulation performance.

A large number, for example 300 to 500, of insertion holes 29 passing through the cap 15 in its thickness direction (in a vertical direction) are formed in the cap 15. An inner diameter of the insertion hole 29 is set to approximately 15 to 25 mm.

The cap is configured such that the sheath tubes 17 are inserted into all these insertion holes 29. As shown in FIG. 4, the sheath tube 17 has a straight tube shape with an outer diameter of 15 to 25 mm, an inner diameter of 13 to 23 mm, and a length of 500 to 700 mm approximately, and the bottom portion thereof reaches the perforated plate 20, and an upper portion thereof opens so as to be exposed on the upper side surface of the cap 15.

The respective upper portions of the sheath tubes 17, which touch the cap 15, are comprised of resin pipes, and portions lower than those are comprised of stainless steel, aluminum alloy, or the like.

Further, a large number of small diameter gas permeable holes 30 are formed in the respective walls of the sheath tubes 17.

A fixing claw (not shown) for fixing the sheath tube 17 to the cap 15 is integrally mounted to the top portion of the sheath tube 17, and the fixing claw is engaged with an engaging concave portion (not shown) formed in the upper edge (the upper board 26) of the insertion hole 29 of the cap 15, to fix the sheath tube 17 to the cap 15, which causes the sheath tube 17 to be not pulled up at the same time of pulling up the ampoule storing tool 16.
(Ampoule Storing Tool)

Figure 5:
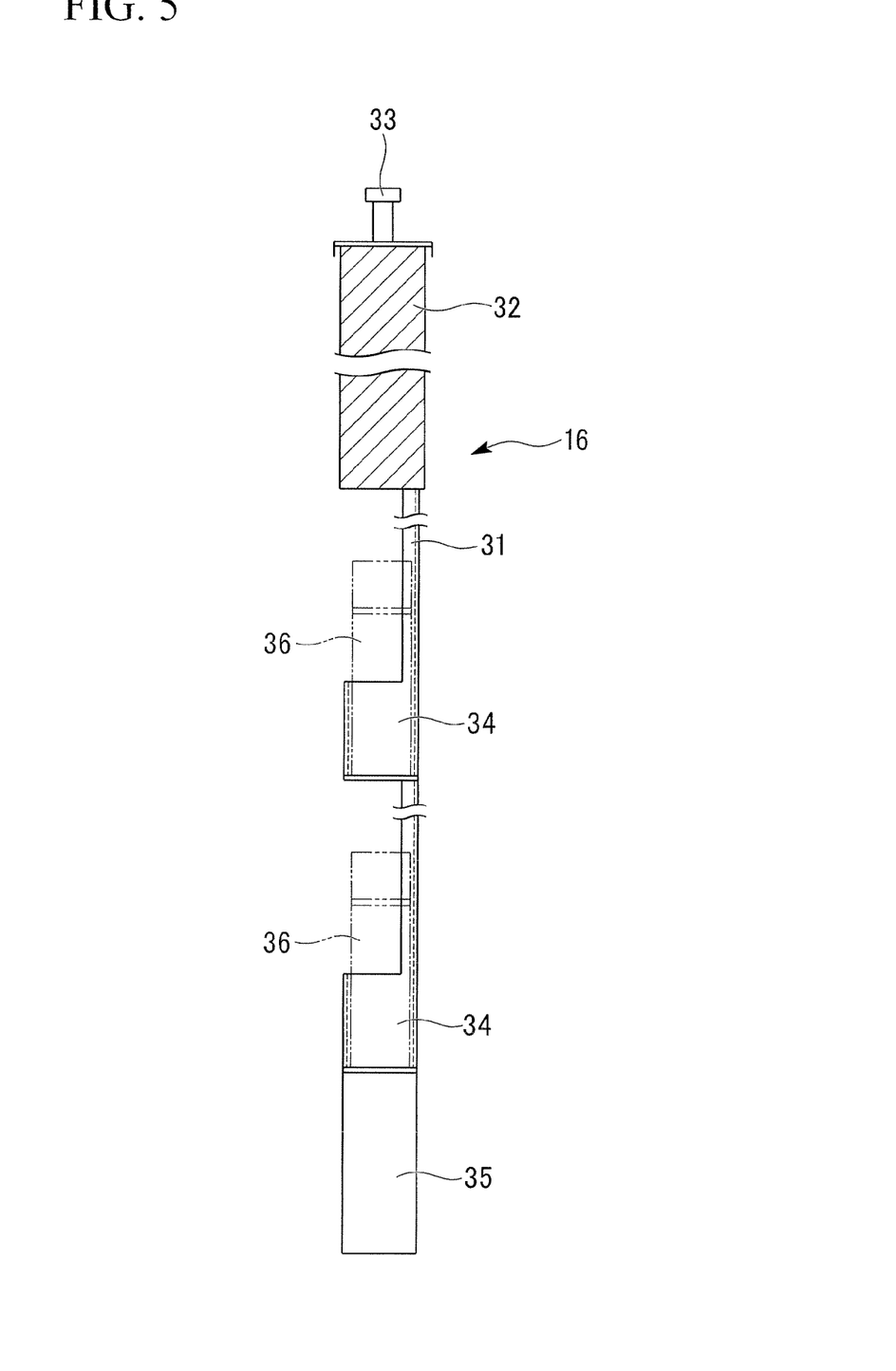
FIG. 5 is a schematic explanatory diagram showing an example of the ampoule storing tool in the present invention.

The ampoule storing tools 16 pass through in a movable manner in a vertical direction in the sheath tubes 17. As shown in FIG. 5, the ampoule storing tool 16 is comprised of a support pillar 31 made of stainless steel, aluminum alloy, or the like, a round-bar thermal insulating section 32 provided in the upper portion of the support pillar 31, a handle portion 33 mounted to the upper portion of the thermal insulating section 32, and a plurality, for example eight, of ampoule storing sections 34 which are arrayed with intervals in a vertical direction of the support pillar 31.

The support pillar 31 has a band shape whose horizontal cross sectional shape is curved to be a circular arc shape, and a guide pipe 35 is provided to the lower end part thereof. This guide pipe 35 is for preventing the ampoule storing tool 16 from failing to be inserted into the cap 15 after pulling up the ampoule storing tool 16 even with the ampoule storing section 34 on the lowermost end. Note that the guide pipe 35 is not necessarily required.

The thermal insulating section 32 is formed such that its outer diameter is substantially the same as the inner diameter of the sheath tube 17, and the length thereof in a vertical direction is substantially the same as the thickness in a vertical direction of the cap 15.

The thermal insulating section 32 is configured such that its interior is made of a synthetic resin such as a glass fiber reinforced epoxy resin and its peripheral portion is formed of a resin foam such as a urethane resin foam, and is high in thermal insulation performance.

As shown in FIG. 5, the support pillar 31 is not located on the central axis of the thermal insulating section, and the support pillar 31 is provided to be continued to the side portion of the thermal insulating section 32.

The ampoule storing section 34 has a bottomed cylindrical cup shape in which one ampoule 36, in which a sample to be cryopreserved is encapsulated, is held and stored, and is integrally provided with the side portion of the support pillar 31. The intervals in the vertical direction of the ampoule storing section 34, are determined so as to generate a gap of approximately 5 to 10 mm between the top portion of the ampoule 36 and the bottom portion of the ampoule storing section 34 thereabove when the ampoule 36 is stored in the ampoule storing section 34.

Further, the ampoule storing section 34 is configured such that its outer diameter is slightly smaller than the outer diameter of the thermal insulating section 32, and is mounted to the support pillar 31 such that its central axis is substantially matched to the central axis of the thermal insulating section 32.

Further, as shown in FIG. 2, a ring-shaped gasket 37 comprised of a cushioning material such as a sponge or rubber is fixed to the upper end portion of the vessel body 14 of the cryopreservation vessel 11, and when the cryopreservation vessel 11 is housed at a stated position of the house 12, the gasket 37 is pressed against the top board 38 of the house 12 (refer to FIG. 1).

When the cryopreservation vessel 11 is housed in the house 12, the door of the house 12 is opened to draw out a tray (not shown) stored in the house 12, and the cryopreservation vessel 11 is placed on the tray to be pushed in the inside thereof. When the cryopreservation vessel 11 reaches the stated position, the cryopreservation vessel 11 is to be fixed so as to be slightly pulled upward, thereby causing the gasket 37 to come into firmly contact with the lower surface of the top board 38.

As shown in FIG. 2, a gas venting pipe 39 is provided to pass through the peripheral edge of the cap 15 of the cryopreservation vessel 11, and a gas venting valve 40 is mounted to the upper portion of the gas venting pipe 39. Thereby, it is possible to extract a low temperature liquefied gas vaporized in the vessel body 14 from the inside of the vessel body 14 and to be capable of maintaining the inside pressure of the vessel body 14 not to be negative.

As shown in FIG. 2, the one ampoule-putting-in/out work hole 29a is provided to the peripheral edge of the cap 15 of the cryopreservation vessel 11. This ampoule-putting-in/out work hole 29a is the through hole such as the insertion hole 29, passing through the cap 15 in its thickness direction (in a vertical direction), into which the ampoule storing tool 16 taken out from the sheath tube 17 by the handling robot 13 is inserted.

The inside of the inner vessel 18 of the vessel body 14 is filled with a low-temperature gas generated due to the evaporation of some of the low-temperature liquefied gas as described above, and the low-temperature gas passes through the gas permeable holes 30 of the sheath tube 17 to flow in the ampoule storing tool 16, to cool down the ampoules 36 held in the ampoule storing tool 16, which is brought into a frozen state.

Thereby, it is possible to store the large number of ampoules 36 in a frozen state, to cryopreserve them.

Note that the ampoules 36 to be housed in the cryopreservation vessel 11 are generally prior-frozen state ampoules. However, the ampoule 36 may be an ampoule in another state.

Further, bar-code labels which are recorded with information such as their identification management numbers and the like are pasted onto the body portions of all the ampoules 36 (not shown).

Regarding the identification management number, the first identification codes (for example, 1, 2, 3, . . . , and n) may be respectively attached to the handle portions 33 of the respective ampoule storing tools 16 or the sheath tubes 17 into which the ampoule storing tools 16 are inserted, the number of the ampoules to be stored in each of the ampoule storing tools 16 may be set to 8, and the second identification codes of A, B, C, . . . , and H may be attached to the eight ampoules 36 in descending order. Then, it is possible to identify and manage one of the ampoules on the basis of an identification management number of for example "2-B".

In the cryopreservation vessel 11 having such a structure, a large number of the ampoules 36 can be housed in one cryopreservation vessel 11 as compared with the conventional technology. Further, since the number of ampoules to be stored in each of the ampoule storing tools 16 is decreased, the number of times of taking out the ampoules to the outside of the cryopreservation vessel 11 at the time of putting-in/out works is greatly decreased, which brings about the advantage in that the frequency of frost formations onto the ampoules is reduced.

(House)

As shown in FIG. 1, the house 12 is a cubic box with a side of for example 1,000 mm, in which the cryopreservation vessel 11 can be housed. The house 12 is configured such that a circular insertion hole is formed in the almost center of the top board 38, so as to be capable of approaching the opening portion of the cryopreservation vessel 11 in the house 12 via the insertion hole from the outside.

Further, a portion of the top board 38, which is in the vicinity of the ampoule-putting-in/out work hole 29a of the cryopreservation vessel 11, stretches out toward the outside, and functions as the work table 38a.

Figure 6:
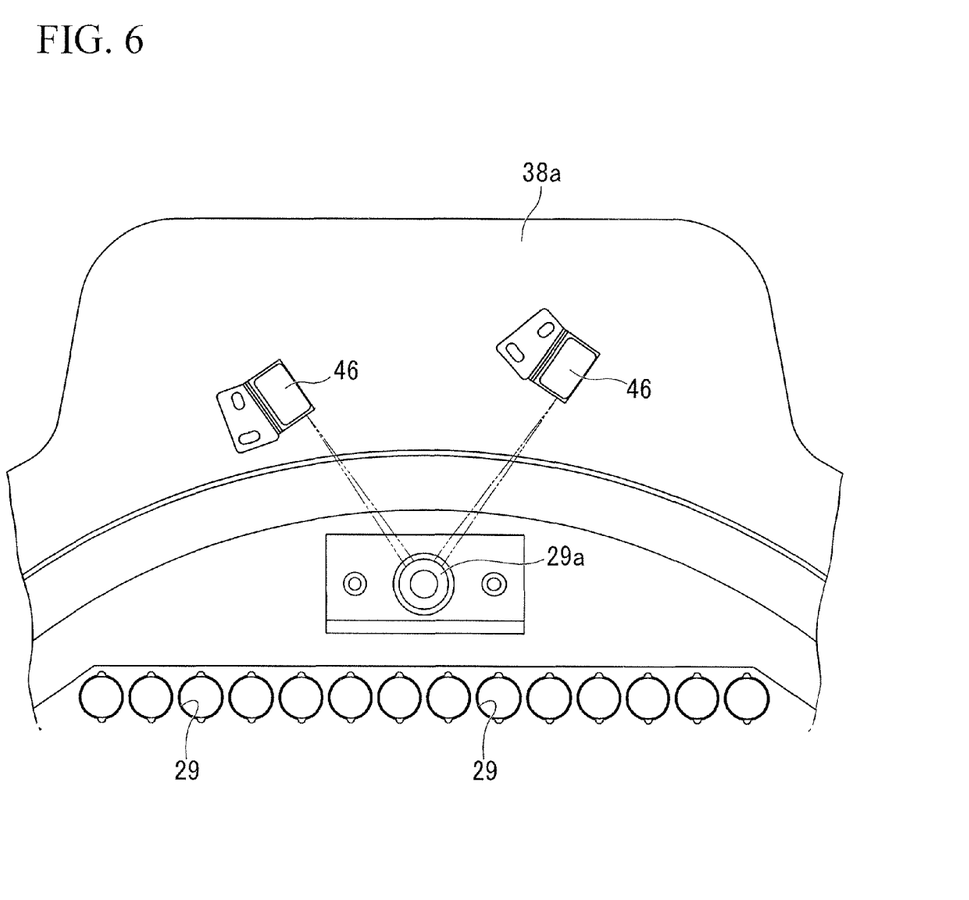
FIG. 6 is a schematic plan view showing the ampoule-putting-in/out work hole in the present invention.

Moreover, as shown in FIG. 6, the work table 38a of the house 12 is equipped with the two bar-code readers 46, 46. These bar-code readers 46 is placed in the vicinity of the ampoule-putting-in/out work hole 29a of the cryopreservation vessel 11, and reads a bar-code of a bar-code label attached to the ampoule 36 of the ampoule storing tools 16 inserted into the ampoule-putting-in/out work hole 29a. In this example, the bar-code readers 46 are placed such that the angle of 100° to 120° is formed by the two imaginary lines which pass through the each bar-code reader 46 and the ampoule 36.

Note that the bar-code reader 46 is not limited to be set in two, and may be one.

Moreover, by open and close the door 41 formed in one side of the house 12, it is possible to take the cryopreservation vessel 11 therein or thereout as described above.

(Handling Robot)

Figure 7:
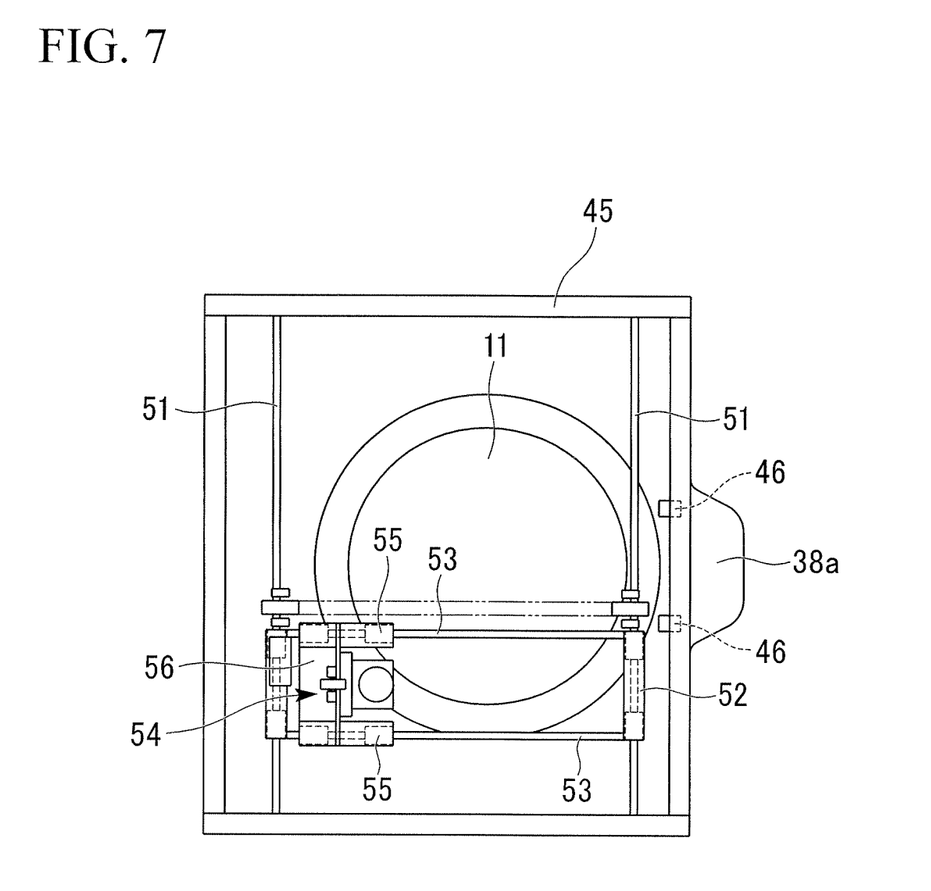
FIG. 7 is a schematic plan view showing an example of the cryopreservation apparatus of the present invention.

As shown in FIG. 1 and FIG. 7, the handling robot 13 is comprised of a robot body 42, an input apparatus 43, and a control apparatus 44.

The frame 45, which is comprised of the four pillars at four corners and the four beams bridging between the consecutive two of these four pillars, is provided on the upper side of the house 12. This frame 45 is equipped with the robot body 42.

That is, a pair of parallel X-axis rails 51, 51 is horizontally attached to the frame 45. The X-axis rail 51 has a smooth round-bar shape for example, and those are respectively placed at one end edge of the frame 45 and the other end edge facing the one edge.

A pair of X-axis trestles 52, 52 that each reciprocates the X-axis rail 51 is mounted to the X-axis rails 51, 51. This X-axis trestle 52 is a hollow cylindrical member, and the X-axis rail 51 passes through the hollow portion of the inside thereof, and the X-axis trestle 52 slides so as to reciprocate in the X-axis direction.

Two round-bar shaped Y-axis rails 53, 53 parallel to each other are bridged so as to connect the pair of X-axis trestles 52, 52. One Y-axis trestle 54 that reciprocates the pair of Y-axis rails 53, 53 is mounted to the pair of Y-axis rails 53, 53.

The Y-axis trestle 54 is comprised of a pair of sliding bodies 55, 55 and a coupling body 56 connecting the pair of sliding bodies 55, 55.

The sliding body 55 is comprised of a hollow cylindrical body, and the Y-axis rail 53 passes through the hollow portion of the inside thereof, and the sliding body 55 slides so as to reciprocate in the Y-axis direction. Thereby, the Y-axis trestle 54 as well reciprocates in the Y-axis direction.

As shown in FIG. 1, one Z-axis rail 57 is mounted to the Y-axis trestle 54 so as to droop. The Z-axis rail 57 is configured such that its leading end portion extends close to the top board 38. A gripper head 58 is mounted so as to be movable up and down to the Z-axis rail 57.

Figure 8:
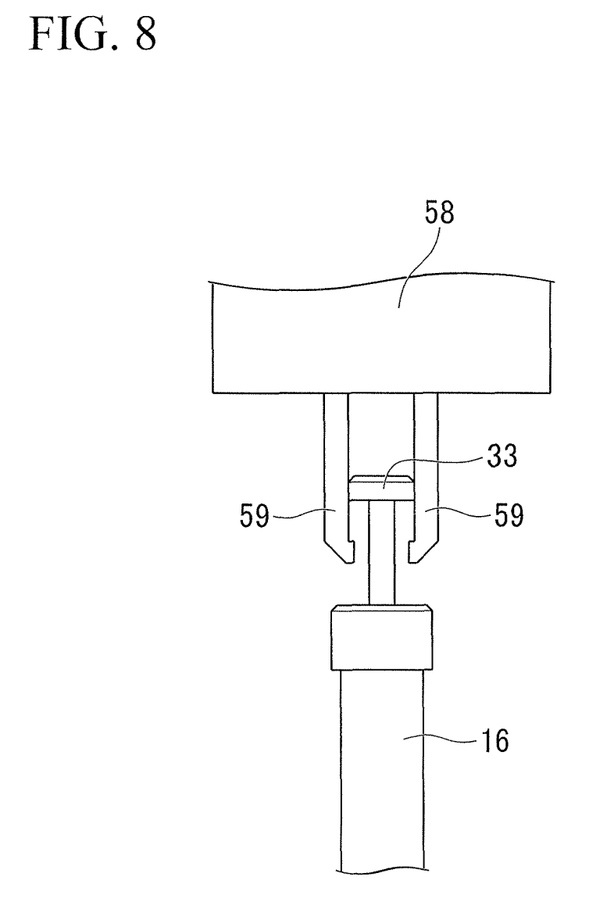
FIG. 8 is a schematic diagram showing the state where the gripping pieces grip the handle portion of the ampoule storing tool in the present invention.

As shown in FIG. 8, a pair of gripping pieces 59, 59 for gripping the handle portion 33 of the ampoule storing tool 16 is provided to the lower surface of the gripper head 58.

The pair of gripping pieces 59, 59 is configured to come close to or be spaced from each other, thereby making it possible to grip or release the handle portion 33.

In this example, the shape of the handle portion 33 is formed to be rectangular columnar. For this reason, the direction of the ampoule storing section 34 of the ampoule storing tool 16 is determined at the time of gripping the handle portion 33 by the gripping pieces 59, 59, and the direction is defined as the side of an operator. Further, it becomes easy to read a bar-code and to take out and store an ampoule.

As shown in FIG. 1, a bar shaped leg portion 61 extending downward is mounted to the Z-axis rail 57. This leg portion 61 is capable of moving up and down along the Z-axis rail 57. An insertion hole for the leg portion 61 is formed in the gripper head 58, which enables the gripper head 58 to move up and down along the Z-axis rail 57 and the leg portion 61. A clamp 60 for gripping the lower end portion of the ampoule storing tool 16 is provided to the lower end portion of the leg portion 61. The upper portion and the lower portion of the ampoule storing tool 16 pulled out from the cryopreservation vessel 11 are respectively gripped by the clamp 60 and the pair of gripping pieces 59, 59. For this reason, the ampoule storing tool 16 is prevented from sliding at the time of moving, and it becomes easy to insert the ampoule storing tool 16 into the ampoule-putting-in/out work hole 29a. Note that, in the case where the gripper head 58 comes close to the place above the cap 3 in order to pull out the ampoule storing tool 16, the leg portion 61 comes down to the lower end of the Z-axis rail 57 and the clamp 60 opens, so as not to interrupt the operation of the gripping pieces 59, 59 of the gripper head 58.

The leg portion 61 is not limited to the above-described example, and may be directly mounted to the gripper head 58. In this case, the shape of the leg portion 61 is formed into a shape which is extensible and shrinkable. Thereby, in the case where the gripper head 58 comes close to the place above the cap 3 in order to pull out the ampoule storing tool 16, the leg portion 61 shrinks above the cap 3 and the clamp 60 opens, so as not to interrupt the operation of the gripping pieces 59, 59 of the gripper head 58.

Further, the clamp 60 may be directly mounted to the Z-axis rail 57. In this case, the clamp 60 is made movable up and down along the Z-axis rail 57. Thereby, in the case where the gripper head 58 comes close to the place above the cap 3 in order to pull out the ampoule storing tool 16, the clamp 60 comes down to the lower end of the Z-axis rail 57 and opens, so as not to interrupt the operation of the gripping pieces 59, 59 of the gripper head 58.

With the above-described structure, the gripper head 58 is capable of freely moving in the three-axis directions that is the X-axis direction, the Y-axis direction, and the Z-axis direction in the work space section. For this reason, it is possible to pull up an arbitrary one of the ampoule storing tools 16 housed in the cryopreservation vessel 11 and further to move up to an arbitrary position.

Such an operation of the gripper head 58 is controlled by a program installed in a control apparatus 44, and the following operation is carried out.

(Operation of Handling Robot)

That is, the program is for executing a series of operations in which, when an identification management number of an ampoule is input to the input apparatus 43, the gripper head 58 pulls out the target ampoule storing tool 16 to hold its lower portion with the clamp 60, and moves the ampoule storing tool 16 in this state up to the place immediately above the ampoule-putting-in/out work hole 29a, and moreover, the gripper head 58 inserts the ampoule storing tool 16 into the ampoule-putting-in/out work hole 29a, and stops when the target ampoule 36 comes to the opening edge of the ampoule-putting-in/out work hole 29a.

The take-out/put-in operation of the ampoule due to the robot is carried out as follows.

First, since the position of the cryopreservation vessel 11 in the house 12 is slightly shifted by taking in or out the cryopreservation vessel 11 in some cases, it is necessary to set a reference point (an original point) of the gripper head 58 in each case.

The reference point is set by carrying out operations for two to three of the ampoule storing tools 16, in which a specified one of the ampoule storing tools 16 is pulled up to a predetermined position from the cryopreservation vessel 11, the gripping pieces 59, 59 of the gripper head 58 are moved to this position, to grip the handle portion 33 by the gripping pieces 59, 59, and the identification management number of the ampoule 36 or the ampoule storing section 34 exposed in this state is input to the control apparatus 44 to carry out teaching. The identification management number is input to the control apparatus 44 by use of an input apparatus 43 such as a graphic panel.

Further, there is a method for the setting as well in which arbitrary reference points (two points) are provided to the upper surface of the cap 15 in advance with respect to the X-Y axis directions, and the positions of the respective ampoule storing tools 16 and the position of the reference points are memorized as their positional relationships in the control apparatus 44 in advance. In the case where the cryopreservation vessel 11 is shifted, the robot (which is visually confirmable by a laser light) is returned to the reference points by fine-tuned driving, to memorize it again. However, the setting method is not limited these methods.

Note that, with respect to the Z-axis, it is possible to handle a slight shift by making the portion under the neck of the handle portion 33 longer. Alternatively, the height of the cryopreservation vessel 11 is adjusted by a level adjuster mounted under foot of the vessel 11, which makes it possible to match the position of the gripping pieces 59, 59 to the position of the handle portion 33.

Hereinafter, the operations in this embodiment will be described.

When an identification management number of an ampoule to be brought out is input to the input apparatus 43, the control apparatus 44 executes the aforementioned program, the gripper head 58 of the handling robot pulls out the target ampoule storing tool 16 from the cryopreservation vessel 11, the lower portion of the ampoule storing tool 16 is held with the clamp 60, and the ampoule storing tool 16 in this state is moved up to the position immediately above the ampoule-putting-in/out work hole 29a.

Next, the ampoule storing tool 16 is inserted into the ampoule-putting-in/out work hole 29a, and when a target ampoule 36 among the plurality of ampoules stored in the ampoule storing tool 16 descends down to the opening edge of the ampoule-putting-in/out work hole 29a, the insertion of the ampoule storing tool 16 is stopped. At this time, the ampoule 36 stored in the ampoule storing tool 16 is to face the side of the work table 38a.

Then, the two bar-code readers 46, 46 read a bar-code of the ampoule 36, to transmit this identification management number to the control apparatus 44.

In the control apparatus 44, the identification management number from the bar-code readers 46, 46 is compared with the identification management number from the input apparatus 43. In the case where the both are matched to one another, it is confirmed that the ampoule is the target ampoule, which is indicated by an indicator lamp, an indicator buzzer, or the like.

The operator confirms this indication, and then takes out the target ampoule from the ampoule storing tool 16.

Next, when the "take-out/put-in completion button" of the input apparatus 43 is pressed, the gripper head 58 pulls out the ampoule storing tool 16 from the ampoule-putting-in/out work hole 29a, and inserts it into the original position (where it was) of the cryopreservation vessel 11. Then, the putting-out work is terminated.

Note that, when the ampoule storing tool 16 is inserted into the original position of the cryopreservation vessel 11 or inserted into the ampoule-putting-in/out work hole 29a, these insertions can be smoother by forming the shapes of the lower portion of the thermal insulating section 32 of the ampoule storing tool 16 and the lower portion of the guide pipe 35 into tapered shapes so as to become thinner than the respective body portions (not shown).

When an ampoule is stored in the ampoule storing tool 16, in the same way as taking-out of an ampoule, the target ampoule storing tool 16 is pulled up from the cryopreservation vessel 11, to be inserted into the ampoule-putting-in/out work hole 29a, and the empty ampoule storing section 34 to be a target is exposed.

In this state, the operator manually stores the ampoule 36 into the empty ampoule storing section 34.

At this time, the bar-code readers 46, 46 read the bar-code attached to the ampoule, the identification management number is transmitted to the control apparatus 44 and compared with the identification management number input to the input apparatus 43, and it is confirmed whether or not the target ampoule is stored in the target ampoule storing section 34. When the operator knows the fact confirmed by an indication as described above, the operator presses the "take-out/put-in completion button" of the input apparatus 44.

Then, the gripper head 58 of the robot pulls out the ampoule storing tool 16 from the ampoule-putting-in/out work hole 29a, and inserts it into the original position of the cryopreservation vessel 11. Then, the putting-in work is terminated, and the gripper head 58 returns to the waiting position.

According to the aforementioned operation, it can be considered that the ampoule storing tool 16 is exposed to the atmosphere and frost is adhered to the ampoule storing tool 16 and the ampoules 36 stored therein while the ampoule storing tool 16 is completely taken out from the insertion hole 29 of the cryopreservation vessel 11, and subsequently, inserted into the ampoule-putting-in/out work hole 29a.

However, the operation between taking the ampoule storing tool 16 out from the insertion hole 29 and the insertion into the ampoule-putting-in/out work hole 29a is carried out by the handling robot 13. Accordingly, the operation is quickly carried out, the time for the exposure to the atmosphere is short, and the frost formation is comparatively hardly to occur.

For these reasons, there are very few problems when the bar-code of the ampoule 36 is read by the bar-code reader 46, and the readability of the bar-code reader 46 itself is improved. Thus, the precise reading is possible.

In this embodiment, as described above, the bar-code attached to the ampoule 36 is certainly and unmistakably read by the bar-code readers 46, 46. Therefore, it is possible to precisely confirm that the ampoule taken out from the ampoule storing tool 16 or stored in the ampoule storing tool 16 is the target one, which makes it possible to prevent confusion of ampoules.

Further, a significant part of the ampoule putting-in/out work, in particular, a work for specifying an ampoule is automatically performed, which greatly reduces a load on an operator.

Moreover, even in the case where an ampoule to be a target is stored in the ampoule storing section 34 in the upper portion of the ampoule storing tool 16, the ampoule existing in this portion is kept in a cooling state because a great part of the ampoule storing tool 16 is located in the cryopreservation vessel 11. Therefore, the frequency of applying wasteful heat to the ampoule is reduced.

Further, in the actual cryopreservation operation of a sample, the cryopreservation apparatus is configured such that the work table 38a of the house 12 faces the side of an operator and the ampoule-putting-in/out work hole 29a is in the vicinity of an operator. In particular, when the cryopreservation vessel 11 is large-sized, it is important in terms of workability to place the ampoule-putting-in/out work hole 29a in the vicinity of an operator.

Moreover, in the case of using a plurality of cryopreservation devices of the present invention, the cryopreservation devices may be arrayed along a wall surface of a room such as a laboratory. Even in such case, when the work table 38a, i.e. the ampoule-putting-in/out work hole 29a is placed on the near side of an operator, workability is good, the cryopreservation devices can be arrayed without spacing, and the small installation space is required.

INDUSTRIAL APPLICABILITY

According to the present invention, it is possible to store a variety of biological samples for a long period and stably in respective research institutes and medical institutions in the biomedical field, medical field, pharmaceutical field, and livestock field.

The invention claimed is:

1. A cryopreservation device comprising:
a cryopreservation vessel;
a house which houses the cryopreservation vessel; and
a handling robot provided on the house, wherein
the cryopreservation vessel comprises a vessel body which holds a low-temperature liquefied gas, a cap which closes an opening section of the vessel body and has a plurality of insertion holes formed to pass through in a vertical direction, sheath tubes which are inserted into the insertion holes of the cap, and ampoule storing tools which are housed so as to be able to pass through the sheath tubes, in which the ampoule storing tools are each comprised of a support pillar and a plurality of ampoule storing sections which are attached to the support pillar so as to be arrayed in a vertical direction of the support pillar, and an ampoule-putting-in/out work hole is formed in the cap so as to pass through in a vertical direction;
the house is used to take the cryopreservation vessel therein or thereout, is adjacent to the opening section of the vessel body, and has a work table provided in the vicinity of the ampoule-putting-in/out work hole;

the handling robot comprises a gripper head, an input apparatus in which an identification management number of a certain ampoule is input, a bar-code reader which is provided on the work table of the house, and a control apparatus which controls a movement of the gripper head on the basis of the identification management number of the bar-code of the certain ampoule from the input apparatus; and upper portions of the sheath tubes, which touch the cap, are comprised of resin pipes, and portions of the sheath tubes lower than the upper portions are comprised of stainless steel or aluminum alloy.

2. A cryopreservation device comprising:

a cryopreservation vessel;

a house which houses the cryopreservation vessel; and a handling robot provided on the house, wherein the cryopreservation vessel comprises a vessel body which holds a low-temperature liquefied gas, a cap which closes an opening section of the vessel body and has a plurality of insertion holes formed to pass through in a vertical direction, sheath tubes which are inserted into the insertion holes of the cap, and ampoule storing tools are each comprised of a support pillar and a plurality of ampoule storing sections which are attached to the support pillar so as to be arrayed in a vertical direction of the support pillar, and an ampoule-putting-in/out work hole is formed in the cap so as to pass through in a vertical direction;

the house is used to take the cryopreservation vessel therein or thereout, is adjacent to the opening section of the vessel body, and has a work table provided in the vicinity of the ampoule-putting-in/out work hole; and the handling robot comprises a gripper head, an input apparatus in which an identification management number of a certain ampoule is input, a bar-code reader which is provided on the work table of the house, and a control apparatus which controls a movement of the gripper head on the basis of the identification management number of the bar-code of the certain ampoule from the input apparatus, wherein the two bar-code readers are provided on the work table, an angle formed by two imaginary lines which pass through the each bar-code reader and the ampoule is within a range from 100° to 120°; and upper portions of the sheath tubes, which touch the cap, are comprised of resin pipes, and portions of the sheath tubes lower than the upper portions are comprised of stainless steel or aluminum alloy.

* * * * *